United States Patent
Lambrecht et al.

(10) Patent No.: US 11,744,656 B2
(45) Date of Patent: Sep. 5, 2023

(54) GEARED GRIP ACTUATION FOR MEDICAL INSTRUMENTS

(71) Applicant: Intuitive Surgical Operations, Inc., Sunnyvale, CA (US)

(72) Inventors: Bram Gilbert Antoon Lambrecht, Sunnyvale, CA (US); Thomas G. Cooper, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 301 days.

(21) Appl. No.: 17/242,918

(22) Filed: Apr. 28, 2021

(65) Prior Publication Data

US 2021/0315648 A1 Oct. 14, 2021

Related U.S. Application Data

(63) Continuation of application No. 16/317,214, filed as application No. PCT/US2017/038343 on Jun. 20, 2017, now Pat. No. 11,007,024.

(60) Provisional application No. 62/362,365, filed on Jul. 14, 2016.

(51) Int. Cl.
*A61B 34/30* (2016.01)
*A61B 17/00* (2006.01)
*A61B 90/00* (2016.01)
*A61B 17/29* (2006.01)

(52) U.S. Cl.
CPC .............. *A61B 34/30* (2016.02); *A61B 17/00* (2013.01); *A61B 2017/00477* (2013.01); *A61B 2017/2943* (2013.01); *A61B 2034/302* (2016.02); *A61B 2090/031* (2016.02)

(58) Field of Classification Search
None
See application file for complete search history.

(56) References Cited

U.S. PATENT DOCUMENTS

| 793,510 | A | | 6/1905 | Cramer et al. |
| 2,091,317 | A | * | 8/1937 | Hill .......................... F16H 55/08 74/462 |
| 2,906,143 | A | | 9/1959 | Musser |

(Continued)

FOREIGN PATENT DOCUMENTS

| CN | 2573759 Y | 9/2003 |
| EP | 2548529 A1 | 1/2013 |

(Continued)

OTHER PUBLICATIONS

US 7,331,907 B2, 02/2008, Lee et al. (withdrawn)

(Continued)

*Primary Examiner* — Christian A Sevilla

(57) ABSTRACT

An actuation mechanism for a medical instrument includes a pinion and a face gear that move a push-pull element. The pinion has a mounting that permits rotation of the pinion by an external control system such as a robot. The face gear meshes with the pinion. The push-pull element may have a proximal end coupled to the face gear and a distal end coupled to a tool at a distal end of an instrument shaft. A manipulator coupled for manual rotation of the actuation mechanism may include a slip clutch to prevent manual application of excessive force to the actuation mechanism.

20 Claims, 9 Drawing Sheets

(56) References Cited

U.S. PATENT DOCUMENTS

| | | | |
|---|---|---|---|
| 3,262,331 A * | 7/1966 | Breuer | F16H 55/0853 |
| | | | 74/462 |
| 4,899,608 A | 2/1990 | Knappe et al. | |
| 5,395,369 A | 3/1995 | McBrayer et al. | |
| 5,601,575 A * | 2/1997 | Measamer | A61B 17/0469 |
| | | | 606/147 |
| 5,674,024 A | 10/1997 | Daumal et al. | |
| 5,792,135 A | 8/1998 | Madhani et al. | |
| 5,807,377 A | 9/1998 | Madhani et al. | |
| 5,876,325 A | 3/1999 | Mizuno et al. | |
| 6,007,550 A | 12/1999 | Wang et al. | |
| 6,318,199 B1 | 11/2001 | Buck | |
| 6,331,181 B1 | 12/2001 | Tierney et al. | |
| 6,371,952 B1 | 4/2002 | Madhani et al. | |
| 6,394,998 B1 | 5/2002 | Wallace et al. | |
| 6,676,684 B1 | 1/2004 | Morley et al. | |
| 6,817,974 B2 | 11/2004 | Cooper et al. | |
| 6,817,998 B2 | 11/2004 | Lahaye | |
| 6,994,708 B2 | 2/2006 | Manzo | |
| 6,997,079 B2 | 2/2006 | Nomura et al. | |
| 7,090,683 B2 | 8/2006 | Brock et al. | |
| 7,169,141 B2 | 1/2007 | Brock et al. | |
| 7,214,230 B2 | 5/2007 | Brock et al. | |
| 7,371,210 B2 | 5/2008 | Brock et al. | |
| 7,524,320 B2 | 4/2009 | Tierney et al. | |
| 7,608,083 B2 | 10/2009 | Lee et al. | |
| 7,666,191 B2 | 2/2010 | Orban, III et al. | |
| 7,691,098 B2 | 4/2010 | Wallace et al. | |
| 7,935,130 B2 | 5/2011 | Williams | |
| 7,963,913 B2 | 6/2011 | Devengenzo et al. | |
| 8,142,421 B2 | 3/2012 | Cooper et al. | |
| 8,316,961 B2 | 11/2012 | Isobe et al. | |
| 8,444,631 B2 | 5/2013 | Yeung et al. | |
| 8,479,969 B2 | 7/2013 | Shelton, IV | |
| 8,506,555 B2 | 8/2013 | Ruiz Morales | |
| 8,551,115 B2 | 10/2013 | Steger et al. | |
| 8,597,280 B2 | 12/2013 | Cooper et al. | |
| 8,771,270 B2 | 7/2014 | Burbank | |
| 8,800,838 B2 | 8/2014 | Shelton, IV | |
| 8,992,565 B2 | 3/2015 | Brisson et al. | |
| 9,028,494 B2 | 5/2015 | Shelton, IV et al. | |
| 9,078,684 B2 | 7/2015 | Williams | |
| 9,121,494 B2 | 9/2015 | Buchleitner | |
| 9,198,714 B2 | 12/2015 | Worrell et al. | |
| 9,204,923 B2 | 12/2015 | Manzo et al. | |
| 9,232,979 B2 | 1/2016 | Parihar et al. | |
| 9,259,274 B2 | 2/2016 | Prisco | |
| 9,259,275 B2 | 2/2016 | Burbank | |
| 9,572,616 B2 | 2/2017 | Vaughn | |
| 9,664,262 B2 | 5/2017 | Donlon et al. | |
| 9,839,439 B2 | 12/2017 | Cooper et al. | |
| 9,913,694 B2 | 3/2018 | Brisson | |
| 9,931,106 B2 | 4/2018 | Au et al. | |
| 10,016,244 B2 | 7/2018 | Cooper et al. | |
| 10,022,193 B2 | 7/2018 | Cooper et al. | |
| 10,076,348 B2 | 9/2018 | Anderson et al. | |
| 10,130,366 B2 | 11/2018 | Shelton, IV et al. | |
| 10,201,365 B2 | 2/2019 | Boudreaux et al. | |
| 10,219,874 B2 | 3/2019 | Yu et al. | |
| 10,288,837 B2 | 5/2019 | Miyatani et al. | |
| 10,314,583 B2 | 6/2019 | Smith et al. | |
| 10,478,256 B2 | 11/2019 | Shelton, IV et al. | |
| 10,543,051 B2 | 1/2020 | Schena et al. | |
| 10,595,949 B2 | 3/2020 | Donlon et al. | |
| 10,624,709 B2 | 4/2020 | Remm | |
| 10,653,489 B2 | 5/2020 | Kopp | |
| 10,667,877 B2 | 6/2020 | Kapadia | |
| 10,682,141 B2 | 6/2020 | Moore et al. | |
| 10,779,898 B2 | 9/2020 | Hill et al. | |
| 10,792,112 B2 | 10/2020 | Kokish et al. | |
| 10,806,530 B2 | 10/2020 | Liao et al. | |
| 11,007,024 B2 | 5/2021 | Lambrecht et al. | |
| 11,013,566 B2 | 5/2021 | Diel et al. | |
| 11,076,926 B2 | 8/2021 | Ragosta et al. | |
| 11,118,661 B2 | 9/2021 | Abbott | |
| 11,517,397 B2 | 12/2022 | Lambrecht et al. | |
| 2002/0111635 A1 | 8/2002 | Jensen et al. | |
| 2005/0042943 A1 | 2/2005 | Mocivnik et al. | |
| 2005/0089345 A1 | 4/2005 | Yasumoto et al. | |
| 2005/0119527 A1 | 6/2005 | Banik et al. | |
| 2007/0043338 A1 | 2/2007 | Moll et al. | |
| 2007/0215825 A1 | 9/2007 | Madden | |
| 2007/0232858 A1 | 10/2007 | Macnamara et al. | |
| 2008/0046122 A1 | 2/2008 | Manzo et al. | |
| 2008/0065102 A1 | 3/2008 | Cooper | |
| 2008/0065105 A1 | 3/2008 | Larkin et al. | |
| 2008/0087871 A1 | 4/2008 | Schena et al. | |
| 2008/0103491 A1 | 5/2008 | Omori et al. | |
| 2008/0196533 A1 | 8/2008 | Bergamasco et al. | |
| 2008/0223903 A1 | 9/2008 | Marczyk | |
| 2009/0088774 A1 | 4/2009 | Swarup et al. | |
| 2009/0110533 A1 | 4/2009 | Jinno et al. | |
| 2009/0198272 A1 | 8/2009 | Kerver et al. | |
| 2010/0011900 A1 | 1/2010 | Burbank et al. | |
| 2010/0170519 A1 | 7/2010 | Romo et al. | |
| 2010/0175701 A1 | 7/2010 | Reis et al. | |
| 2010/0318101 A1 | 12/2010 | Choi et al. | |
| 2011/0015650 A1 | 1/2011 | Choi et al. | |
| 2011/0071543 A1 | 3/2011 | Prisco et al. | |
| 2011/0118754 A1 | 5/2011 | Dachs, II et al. | |
| 2011/0277775 A1 | 11/2011 | Holop et al. | |
| 2011/0295269 A1 | 12/2011 | Swensgard et al. | |
| 2011/0295270 A1 | 12/2011 | Giordano et al. | |
| 2012/0046522 A1 | 2/2012 | Naito | |
| 2012/0109186 A1 | 5/2012 | Parrott et al. | |
| 2012/0123441 A1 | 5/2012 | Au et al. | |
| 2012/0239060 A1 | 9/2012 | Orban, III et al. | |
| 2012/0289974 A1 | 11/2012 | Rogers et al. | |
| 2012/0298719 A1 * | 11/2012 | Shelton, IV | A61B 34/30 |
| | | | 227/176.1 |
| 2013/0046318 A1 | 2/2013 | Radgowski et al. | |
| 2013/0123783 A1 | 5/2013 | Marczyk et al. | |
| 2013/0144395 A1 | 6/2013 | Stefanchik et al. | |
| 2014/0005678 A1 | 1/2014 | Shelton, IV et al. | |
| 2014/0005708 A1 | 1/2014 | Shelton | |
| 2014/0100558 A1 | 4/2014 | Schmitz et al. | |
| 2014/0257333 A1 | 9/2014 | Blumenkranz | |
| 2014/0276723 A1 * | 9/2014 | Parihar | A61B 17/07207 |
| | | | 606/33 |
| 2015/0005786 A1 | 1/2015 | Burbank | |
| 2015/0051034 A1 | 2/2015 | Cooper et al. | |
| 2015/0150635 A1 | 6/2015 | Kilroy et al. | |
| 2015/0150636 A1 | 6/2015 | Hagn et al. | |
| 2015/0157355 A1 | 6/2015 | Price et al. | |
| 2016/0058443 A1 | 3/2016 | Yates et al. | |
| 2016/0151115 A1 | 6/2016 | Karguth et al. | |
| 2016/0184034 A1 | 6/2016 | Holop et al. | |
| 2016/0184036 A1 | 6/2016 | Solomon et al. | |
| 2016/0184037 A1 | 6/2016 | Cooper et al. | |
| 2016/0199138 A1 | 7/2016 | Cooper et al. | |
| 2016/0296219 A1 | 10/2016 | Srivastava et al. | |
| 2016/0361049 A1 | 12/2016 | Dachs, II et al. | |
| 2017/0007345 A1 | 1/2017 | Smith et al. | |
| 2017/0172672 A1 | 6/2017 | Bailey et al. | |
| 2017/0165017 A1 | 8/2017 | Chaplin et al. | |
| 2018/0055583 A1 | 3/2018 | Schuh et al. | |
| 2018/0229021 A1 | 8/2018 | Donlon et al. | |
| 2018/0243036 A1 | 8/2018 | Donlon et al. | |
| 2019/0038282 A1 | 2/2019 | Shelton, IV et al. | |
| 2019/0099227 A1 | 4/2019 | Rockrohr | |
| 2019/0117325 A1 | 4/2019 | Kishi | |
| 2019/0125468 A1 | 5/2019 | Adams | |
| 2019/0231451 A1 | 8/2019 | Lambrecht et al. | |
| 2019/0231464 A1 | 8/2019 | Wixey et al. | |
| 2019/0239965 A1 | 8/2019 | Abbott | |
| 2019/0249759 A1 | 8/2019 | Abbott | |
| 2019/0298323 A1 | 10/2019 | Lambrecht et al. | |
| 2019/0307522 A1 | 10/2019 | Lambrecht et al. | |
| 2019/0328467 A1 | 10/2019 | Waterbury et al. | |
| 2020/0197117 A1 | 6/2020 | Donlon et al. | |
| 2020/0261168 A1 * | 8/2020 | Anglese | B25J 9/104 |
| 2020/0315718 A1 * | 10/2020 | Harris | A61B 34/30 |
| 2021/0220062 A1 | 7/2021 | Lambrecht et al. | |
| 2021/0322118 A1 | 10/2021 | Donlon et al. | |

(56) References Cited

U.S. PATENT DOCUMENTS

| | | |
|---|---|---|
| 2021/0372508 A1 | 12/2021 | Abbott |
| 2022/0000572 A1 | 1/2022 | Ragosta et al. |
| 2022/0192764 A1 | 6/2022 | Waterbury et al. |

FOREIGN PATENT DOCUMENTS

| | | |
|---|---|---|
| EP | 2783643 A1 | 10/2014 |
| EP | 3103374 A1 | 12/2016 |
| EP | 3195993 A1 | 7/2017 |
| JP | H06114000 A | 4/1994 |
| JP | H10249777 A | 9/1998 |
| JP | 2003024336 A | 1/2003 |
| JP | 2005288590 A | 10/2005 |
| WO | WO-9729690 A1 | 8/1997 |
| WO | WO-0030557 A1 | 6/2000 |
| WO | WO-2012068156 A2 | 5/2012 |
| WO | WO-2015023772 A1 | 2/2015 |
| WO | WO-2015142290 A1 | 9/2015 |
| WO | WO-2016073637 A1 | 5/2016 |
| WO | WO-2016161449 A1 | 10/2016 |
| WO | WO-2016172299 A1 | 10/2016 |
| WO | WO-2016189284 A1 | 12/2016 |
| WO | WO-2017188851 A1 | 11/2017 |
| WO | WO-2018013313 A1 | 1/2018 |
| WO | WO-2018049217 A1 | 3/2018 |
| WO | WO-2018094191 A1 | 5/2018 |
| WO | WO-2020252184 A1 | 12/2020 |

OTHER PUBLICATIONS

International Search Report and Written Opinion for Application No. PCT/US2017/038343, dated Oct. 20, 2017, 9 pages.

Litvin F.L., et al., "Face Gear Drive with Helical Involute Pinion: Geometry, Generation by a Shaper and a Worm, Avoidance of Singularities and Stress Analysis," NASA/CR—2005-213443, ARL-CR-557, Feb. 2005, 62 pages.

Litvin F.L., et al., "Handbook on Face Gear Drives with a Spur Involute Pinion," NASA/CR-2000-209909, ARL-CR-447, Mar. 2000, 106 pages.

Smith L.J., "The Involute Helicoid and the Universal Gear," Gear Technology, Nov./Dec. 1990, pp. 18-27.

Stadtfeld H, Dr., "Tribology Aspects in Angular Transmission Systems: Part I—General Explanations on Theoretical Bevel Gear Analysis," Gear Technology, Aug. 2010, URL: https://www.geartechnology.com/issues/0810x/stadtfeld1.pdf, pp. 46-52.

Stadtfeld H, Dr., "Tribology Aspects in Angular Transmission Systems: Part II—Straight Bevel Gears," Gear Technology, Sep.-Oct. 2010, URL: http://www.geartechnology.com/issues/0910x/stadtfeld.pdf, pp. 47-52.

Stadtfeld H, Dr., "Tribology Aspects in Angular Transmission Systems: Part III—Zerol Bevel Gears," Gear Technology, Nov.-Dec. 2010, URL: http://www.geartechnology.com/issues/1110x/zerol.pdf , pp. 42-47.

Stadtfeld H, Dr., "Tribology Aspects in Angular Transmission Systems: Part IV—Spiral Bevel Gears," Gear Technology, Jan.-Feb. 2011, URL: https://www.geartechnology.com/issues/0111x/stadtfeld.pdf, pp. 66-72.

Stadtfeld H, Dr., "Tribology Aspects in Angular Transmission Systems: Part V—Face Gears," Gear Technology, Mar.-Apr. 2011, URL: http://www.geartechnology.com/issues/0311x/stadtfeld.pdf, pp. 47-52.

Stadtfeld H, Dr., "Tribology Aspects in Angular Transmission Systems: Part VI—Beveloid & Hypoloid Gears," Gear Technology, May 2011, URL: https://www.geartechnology.com/issues/0511x/beveloid.pdf, pp. 48-52.

Stadtfeld H, Dr., "Tribology Aspects in Angular Transmission Systems: Part VII—Hypoid Gears," Gear Technology, Jun.-Jul. 2011, URL: https://www.geartechnology.com/issues/0611x/hypoid.pdf, pp. 68-72.

Stadtfeld H, Dr., "Tribology Aspects in Angular Transmission Systems: Part VIII—Super-Reduction Hypoid Gears," Gear Technology, Aug. 2011, URL: http://www.geartechnology.com/issues/0811xZsuperhypoid.pdf, pp. 42-48.

Vertut, Jean and Phillipe Coiffet, Robot Technology; Teleoperation and Robotics Evolution and Development, English translation, Prentice-Hall, Inc., Inglewood Cliffs, NJ, USA 1986, vol. 3A, 332 pages.

\* cited by examiner ance with an aspect of the invention, a grip
GEARED GRIP ACTUATION FOR MEDICAL INSTRUMENTS

RELATED APPLICATIONS

This patent application is a continuation of U.S. application Ser. No. 16/317,214 (filed Jan. 11, 2019), entitled "GEARED GRIP ACTUATION FOR MEDICAL INSTRUMENTS," which is a U.S. national stage filing under 35 U.S.C. § 371 of International Application No. PCT/US2017/038343 (filed Jun. 20, 2017), entitled "GEARED GRIP ACTUATION FOR MEDICAL INSTRUMENTS," which claims priority to and the benefit of the filing date of U.S. Provisional Patent Application No. 62/362,365 (filed Jul. 14, 2016), entitled "GEARED GRIP ACTUATION FOR MEDICAL INSTRUMENTS," each of which is incorporated by reference herein in its entirety.

BACKGROUND

Minimally-invasive medical procedures often employ medical instruments having a tool or end effector or other manipulation element at the distal end of an elongated instrument shaft. During a minimally-invasive medical procedure, the distal ends of one or more such medical instruments may be inserted through one or more small incisions and/or natural lumens to position the distal tools at a work site in a patient. A surgeon or other medical personnel may then control the tools to perform desired clinical functions, e.g., endoscopy, laparoscopy, arthroscopy, hypodermic injection, air-pressure injection, subdermal implants, refractive surgery, percutaneous surgery, cryosurgery, microsurgery, keyhole surgery, endovascular surgery such as angioplasty, coronary catheterization, placement of internal electrodes, and stereotactic surgery, at the work site.

The manipulations required or desired to effectively complete medical procedures can be complex and intricate. Accordingly, medical instruments for minimally-invasive medical procedures may need to provide precise control of many degrees of freedom of movement. One common degree of freedom that may be required for a medical instrument is grip. For example, a surgeon may need an instrument with a distal tool capable holding, moving, clamping, cutting, or cauterizing of target tissue, and such distal tool may accordingly need to close (or open) a grip mechanism such as a clamp or scissors. In a medical instrument, the mechanics for actuation of grip may benefit from being compact to allow space for other mechanisms that control other degrees of freedom movement of the instrument.

SUMMARY

In accordance with an aspect of the invention, a grip actuation mechanism uses a face gear and pinion to push and pull a grip drive element.

One specific implementation is a medical system containing an actuation mechanism. An actuation mechanism may include a pinion and a face gear coupled to move a push-pull element. The pinion has a mounting that permits rotation of the pinion by an external control system such as a robot. The face gear meshes with the pinion. The push-pull element may have a proximal end coupled to the face gear and a distal end coupled to a tool at a distal end of an instrument shaft. A manipulator coupled for manual rotation of the actuation mechanism may include a slip clutch to prevent manual application of excessive force to the actuation mechanism.

Another specific implementation is a medical instrument including a tool, an actuation mechanism, and a manipulator. The actuation mechanism may be coupled to the tool and may have an engagement feature shaped to engage an actuator in a robot, so that rotation of the engagement feature actuates a portion of the tool. The manipulator, which couples to the actuation mechanism so that rotation of the manipulator actuates a portion of the tool, may include a slip clutch that limits the torque manually applied to the actuation.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

Figure 1:
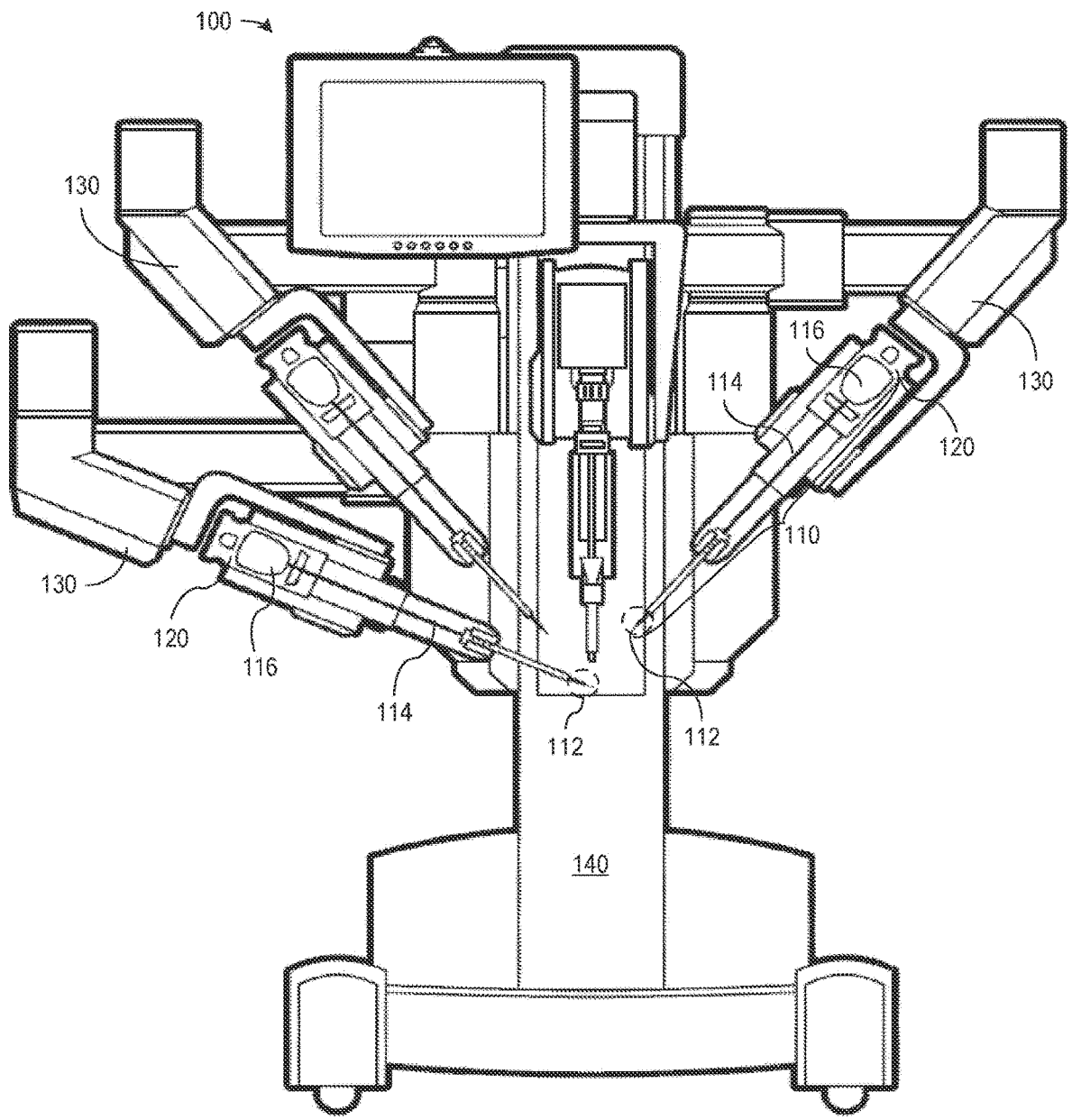
FIG. 1 shows a robotic system that can deploy and operate multiple medical instruments.

An actuation mechanism for an instrument such as a medical instrument may include a gear structure including a face gear and a pinion for precision driving of back-and-forth movement such as grip motion in the instrument. The face gear and pinion may be relatively simple to mold or cut and may be arranged in a compact configuration that is tolerant of misalignment during assembly. The gear structure may also allow flexibility for different arrangement of rotation axes of an instrument input and the face gear. The face gear arrangement may further allow for a high gear ratio when driving a grip mechanism and may still provide low driving friction that allows the grip actuation mechanism to be back driven, i.e., allows the gear structure to move in response to a movement of the grip mechanism.

The grip actuation mechanism may reside in proximal portion of an instrument such as a medical instrument, sometimes referred to herein as the backend of the instrument. The grip actuation mechanism may particularly connect to an elongated push-pull element having a proximal end coupled to the actuation mechanism and a distal end coupled to a grip mechanism at the distal end of an elongate instrument shaft of an instrument. In one implementation, the proximal end of the push-pull element couples to a face gear in the actuation mechanism, and an input spindle shaped to engage an actuator such as a drive motor in a robotic system may include or may be coupled to rotate a pinion that meshes with the face gear. Rotation of the input spindle rotates the pinion and face gear, which may then push or pull the push-pull element and thereby drive closing or opening of the grip mechanism at the distal end of the instrument. In this description, the root term robot and its derivatives include teleoperated systems that use technology associated with robotics, such as a mechanically grounded or hand-held teleoperated surgical system. In addition, the term manipulator and its derivatives include any means—motor or manual—for conveying force or torque to move a mechanical object (manipulator is a term of art in robotics, and in this description it includes manual equivalents).

The actuation mechanism may further permit manual operation or actuation of grip motion. In particular, users of an instrument such as a medical instrument may need to manually open or close the jaws of the instrument when the instrument is in hand instead of being attached to a robotic or other computer-assisted system, and the grip actuation mechanism may further include a manipulator such as a knob, handle, or lever that is connected for manual rotation of the pinion and opening or closing of the jaws. A slip clutch or torque limiter may connect the manipulator to the pinion. The slip clutch may be particularly desirable when an instrument includes a push-pull element such as a rod, wire, or cable that is thin, structurally weak, or runs through relatively weak guide. In such cases, pushing the push-pull element with too much force may cause the push-pull element (with or without a guide) to buckle or kink. While a robotic system may be programmed to monitor and limit the force that the robotic system applies to a push-pull element, users of the system may not be able to properly judge manually applied forces. The slip clutch may limit manually applied force to avoid damage and may still permit manual driving of back-and-forth movement in an instrument.

Although the above examples and other discussions herein often refer to medical procedures and medical instruments, the techniques disclosed also apply to non-medical procedures and non-medical instruments.

FIG. 1 shows an example of a medical system 100 using multiple medical instruments 110, some or all of which may include a grip actuation mechanism disclosed herein. System 100, which may, for example, include a da Vinci® Surgical System commercialized by Intuitive Surgical, Inc., and may particularly employ multiple instruments 110, each of which 1s replaceable and mounted in a docking port 120 on a manipulator arm 130 of a robot 140. A sterile barrier (not shown) including a drape and adaptors for instruments 110 may be between instruments 110 and robot 140, so that robot 140, including manipulator arms 130 and docking ports 120, is outside a sterile environment for a patient. Accordingly, robot 140 may not need to be sterilized between medical procedures. In contrast, instruments 110, which may be used inside the sterile environment and may contact the patient, are compact and removable so that instruments 110 may be cleaned and sterilized or replaced between medical procedures performed using system 100.

Instruments 110 may vary in structure and purpose but may still be interchangeable and have a standard engagement interface, so that different types of instruments 110 may be mounted in docking ports 120 of robot 140 as needed for a particular medical procedure. Instruments 110 may also be changed during a medical procedure to provide the different clinical functions as needed. Each instrument 110 generally includes an end effector or distal tool 112, an elongated instrument shaft 114, and a backend 116. Distal tools 112 may have different designs to implement many different functions. For example, some distal tools 112 for instruments 110 that may provide grip motion may include forceps, graspers, scissors, or cautery tools, which may come in different shapes or sizes. In general, instruments 110 having different distal tools 112 may be mounted on different arms 130 of robot 140 and may work cooperatively in the same work site, although not all distal tools 112 need to provide gripping action. An endoscopic camera, for example, a stereoscopic camera, can also be mounted on an arm to provide visual information, particularly images, of the work site in which distal tools 112 of instruments 110 may be operating.

Docking ports 120 may include actuators such as drive motors that provide mechanical power for actuation of mechanical structures in instruments 110, drive couplings that connect the actuators to inputs of instruments 110, and systems for establishing and maintaining of a sterile barrier between instruments 110 and the rest of medical system 100. Docking ports 120 may additionally include an electrical interface to provide power to instruments 110, e.g., for cautery tools, or for communication with instruments 110, e.g., to identify the type of instrument 110 in a docking port 120, to access parameters of a docked instrument 110, or to receive information from sensors in a docked instrument 110. For example, the electrical interface may provide a high frequency AC voltage that a medical instrument 110 applies to both of the jaws in a distal cautery tool for a monopolar cauterization process, or the electrical interface may provide opposite polarity electrical signals that a medical instrument 110 applies to electrically-isolated, opposing jaws for a bipolar cauterization process. A computer system, which may be connected to or part of robot 140 and connected to a user interface device (not shown), may receive the information from instruments 110 and receive user commands from a surgeon or other medical personnel and may execute software that controls arms 130 and the actuators in docking ports 120 as needed to mechanically actuate and electrically power systems in instruments 110 as needed to execute to the user commands.

Figure 2A:
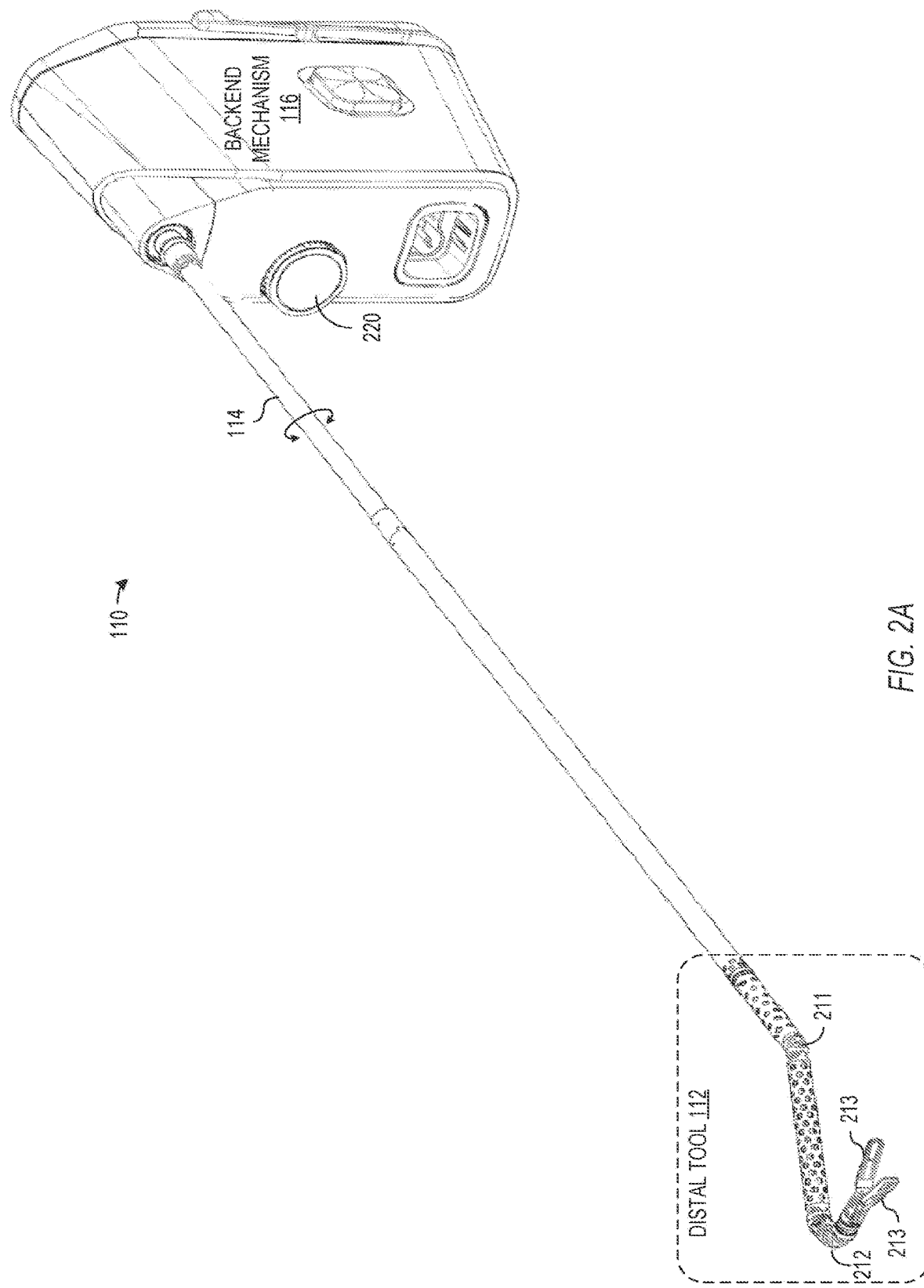
FIG. 2A and FIG. 2B respectively show perspective and top views of an example implementation of a medical instrument.
Figure 2B:
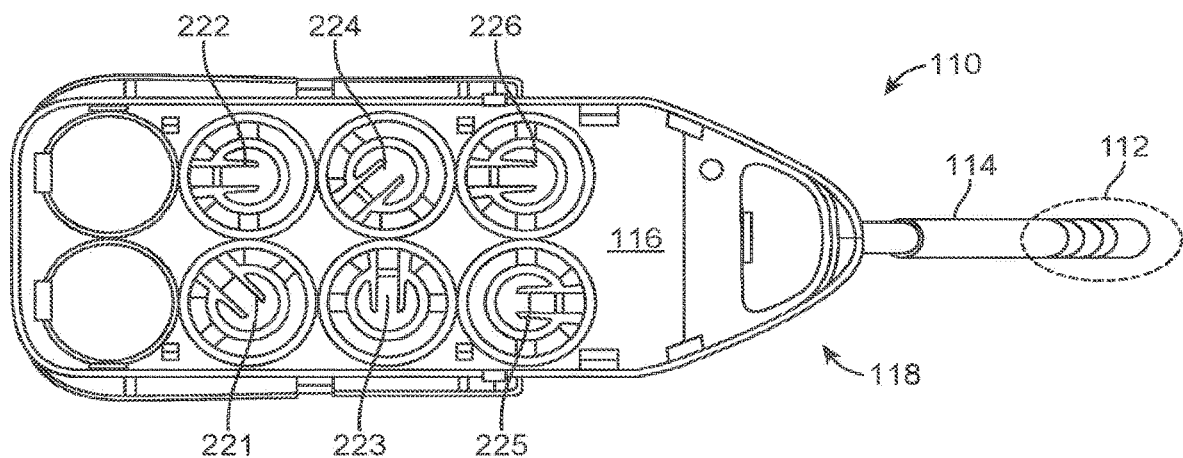

FIGS. 2A and 2B respectively illustrate perspective and top views of an example implementation of a medical instrument 110 suitable for use in medical system 100 of FIG. 1. As shown in FIG. 2A, medical instrument 110 includes a tool 112 at the distal end of an elongated instrument shaft 114 that extends from a backend 116. Distal tool 112 and instrument shaft 114 may have multiple degrees of freedom of movement relative to backend 116, and in the illustrated configuration of FIG. 2A, medical instrument 110 has six degrees of freedom corresponding to: two types of actuation of a first joint mechanism 211; two more types of actuation of a second joint mechanism 212; opening or closing movement of jaws 213; and rotations of instrument shaft 114 about its central or length axis. First joint mechanism 211 and second joint mechanism 212 may also be termed first joint 211 and second joint 212, respectively. In some embodiments, a first wrist comprises first joint 211, and a second wrist comprises second joint 212. Other implementations of medical instruments may provide more, fewer, or different degrees of freedom of movement.

Backend 116 as shown in FIG. 2B has six input spindles 221 to 226 with exterior engagement features that are shaped and positioned to engage actuators in a docking port of a robotic system, e.g., to engage drive motors in docking ports 120 of robot 140 as shown in FIG. 1. In this specific example, first and second actuators in the robot may rotate input spindles 221 and 222 to control actuation of wrist or joint 211. Third and fourth actuators in the robot may rotate input spindles 223 and 224 to control actuation of wrist or joint 212. A fifth actuator may rotate input spindle 225 to control opening or closing 205 of jaws 213, and a sixth actuator may rotate input spindle 226 to control roll rotation of instrument shaft 114. In accordance with one aspect disclosed herein, backend 116 includes a grip actuation mechanism that may act as a transmission to convert the rotation of input spindle 225 into movement that opens or closes jaws 213 or to control a pressure that jaws 213 may apply when opening or closing. Backend 116 also includes a manipulator 220 that permits manual rotation of input spindle 225 for manual control of jaws 213.

Figure 3A:
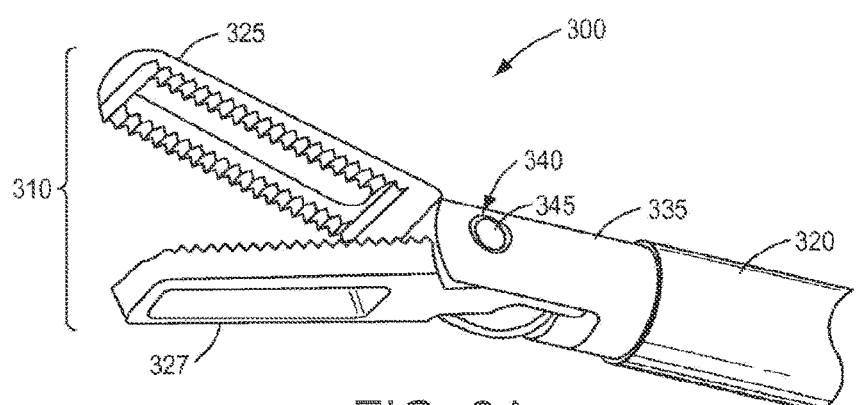
FIG. 3A shows a perspective view of an example implementation of a grip mechanism.
Figure 3B:
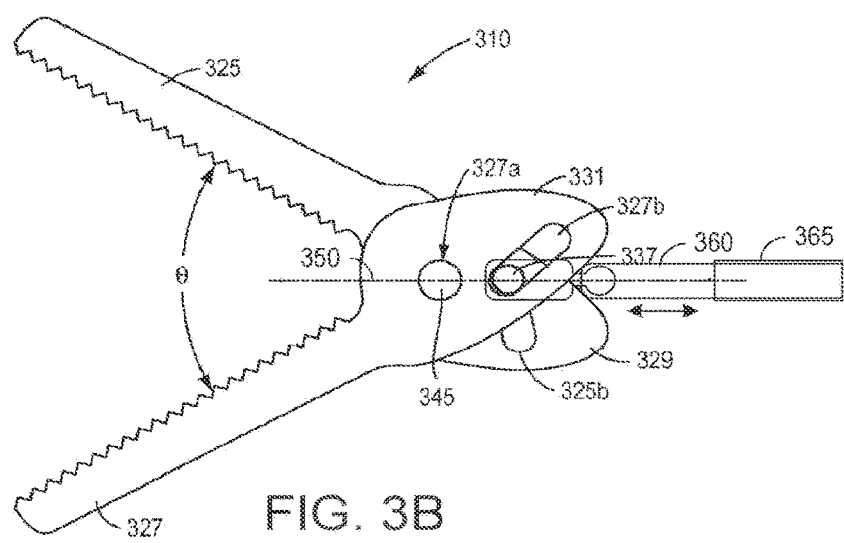
FIG. 3B shows some components of the grip mechanism of FIG. 3A.

FIG. 3A shows an implementation of a distal grip mechanism 300 for one example of a distal tool such as distal tool 112 of FIGS. 1, 2A, and 2B Alternatively, any actuated mechanism that requires driving of opening and closing or back-and-forth movement may be similarly employed and actuated as disclosed herein. In the specific example FIGS. 3A and 3B, grip mechanism 300 includes a pair of jaws 310 mounted on an end portion 320 of a distal tool or at the distal end of instrument shaft 114 with or without intervening wrist mechanisms such as joints 211 or 212 shown in FIG. 2A. Jaws 310 may include a first jaw member 325 and a second jaw member 327 configured to move between an open position and a closed position. Each jaw member may have a range of motion from about O degrees to about 30 degrees, providing a full range of motion for the jaws 310 from about O degrees to about 60 degrees. A grip angle 8 as shown in FIG. 3B may be defined as the angle between faces of the jaw members 325 and 327. When jaw members 325 and 327 are touching one another, such that the faces of both jaw members extend along centerline 350, the grip angle 8 is approximately O degrees, and the jaws are in a closed position. When the jaw members are fully spaced away from one another, the jaws are in a fully open position, and the grip angle 8 may be approximately 60 degrees. This range of "grip motion" is intended to be exemplary only, and the range of grip motion in different implementations of a grip mechanism can be larger or smaller based upon the intended use of the instrument and may depend upon the structure of the jaw members, the manner of connection of the jaw members, and/or the manner of actuation of the jaw members.

FIG. 3B shows how each jaw member 325 or 327 may include a proximal extension 329 or 331, and FIG. 3A shows proximal extensions 329 and 331 mounted in a clevis 335. In some embodiments, proximal extensions 329 and 331 may each comprise a jaw extension. Clevis 335 supports grip mechanism 300 and connects grip mechanism 300 to adjacent portion 320 of the medical instrument, e.g., as jaws 213 connect to wrist mechanisms 212 and 211 and instrument shaft 114 as shown in FIG. 2A. In the implementation of FIGS. 3A and 3B, a clevis pin 345 extends through holes 340 in the sides of clevis 335 and through holes 325a and 327a in proximal extensions 329 and 331 to pivotally couple jaw members 325 and 327 to clevis 335, permitting the jaws to open and close as they pivot about pin 345. In addition, proximal extensions 329 and 331 may include respective cam slots 325b and 327b through which a pin 337 moves during the opening and closing of the jaws 310. Pin 337 particularly connects to and moves with a push-pull element 360 that extends from pin 337 and through the instrument shaft to connect to a grip actuation mechanism in the backend of the medical instrument. Push-pull element 360 may include one or more sections of a relatively rigid structure such as a rod and one or more sections of a more flexible structure such as a cable or wire in a guide or sheath 365 that supports and guides push-pull element 360. A flexible section of push-pull element 360 with guide or sheath 365 may allow driven opening and closing grip mechanism 300 even when push-pull element 360 must be able to flex or bend, for example, where element 360 passes through actuated joints 211 or 212 of FIG. 2A. In operation, a grip actuation mechanism in the backend of a medical instrument connects to push-pull element 360 and may push or pull push-pull element 360 to cause jaws 310 to open or close.

Figure 4A:
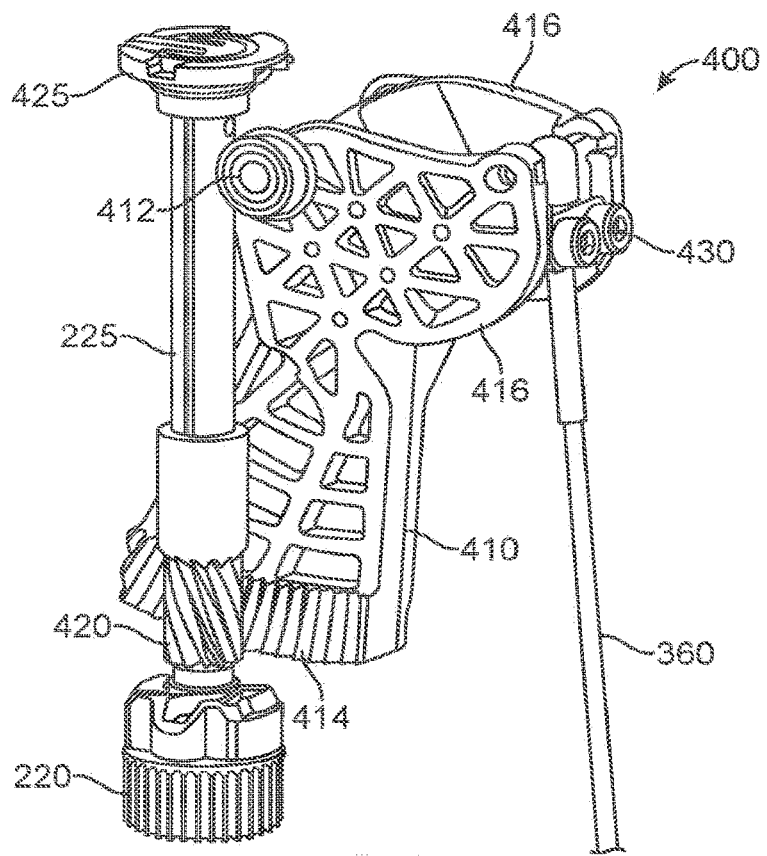
FIG. 4A and FIG. 4B respectively show front and back perspective views of an example implementation of an actuation mechanism.
Figure 4B:
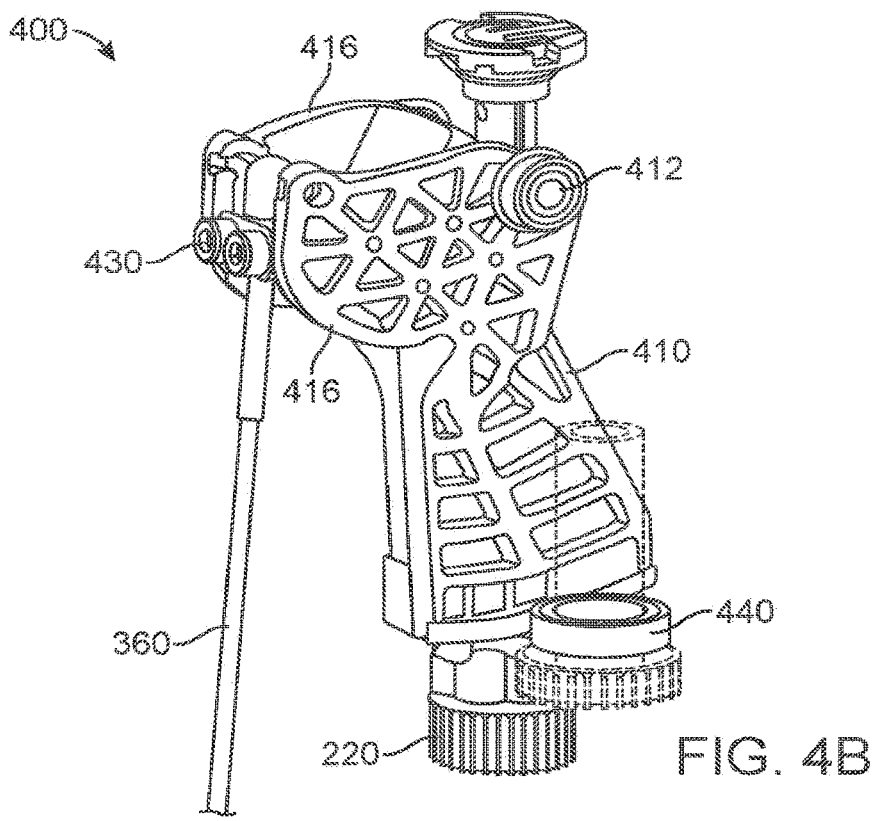

FIGS. 4A and 4B show front and back perspective views of one implementation of an actuation mechanism 400, which includes a face gear 410 and an input gear or pinion 420. Face gear 410 has a shaft 412 that defines a rotation axis of face gear 410 and may ride in bearings mounted in or on the chassis of the instrument backend containing grip actuation mechanism 400. Face gear 410 may particularly be mounted on a chassis in a manner that permits back-and-forth rotation of face gear 410 over a limited angular range about shaft 412. Face gear 410 may be a sector gear with a toothed portion 414 that only subtends a limited angle, e.g., about 32 degrees, depending on the desired range of motion of face gear 410. A connector 430 attaches push-pull element 360 to face gear 410, so that the small angle rocking motion of face gear 410 primarily moves push-pull element 360 along a length axis of the instrument shaft through which push-pull element 360 passes. In general, the diameter of face gear 410 and the moment arm relative to shaft 412 at which connector 430 attaches to face gear 410 may be selected or designed to provide a desired range of motion of push-pull element 360 and provide a desired gear ratio or mechanical advantage when pinion 420 acts on face gear 410.

Pinion 420 meshes with toothed portion 414 on a front side of pinion 420, and a support bearing 440 as shown in FIG. 4B may be used on a back side of pinion 420 and opposing input pinion 420 to ensure that teeth of gears 410 and 420 remain engaged even under high loads. Pinion 420 may be mounted on or otherwise coupled to input spindle 225 so that pinion 420 rotates when a control system rotates input spindle 225. In particular, input spindle 225 includes an engagement feature 425 shaped to engage an actuator, e.g., a drive motor, in an instrument docking port of a robotic system, so that the robotic system may operate the actuator to rotate input spindle 225 and pinion 420 to control movement of push-pull element 360 and to thereby control opening and closing of a grip mechanism attached to push-pull element 360. A manipulator 220, e.g., a knob, handle, lever, or other structure capable of being manually turned, also connects to pinion 420 so that a user can manually rotate manipulator 220 and pinion 420 to move face gear 410 and push-pull element 360 and manually open or close the distal grip mechanism, e.g., grip mechanism 300 of FIG. 3A. As described further below, a slip clutch or torque limiter may connect manipulator 220 to pinion 420 or input spindle 225 to limit the maximum torque or force that a user can manually apply for at least one direction of motion, e.g., for pushing, of push-pull element 360.

Figure 4C:
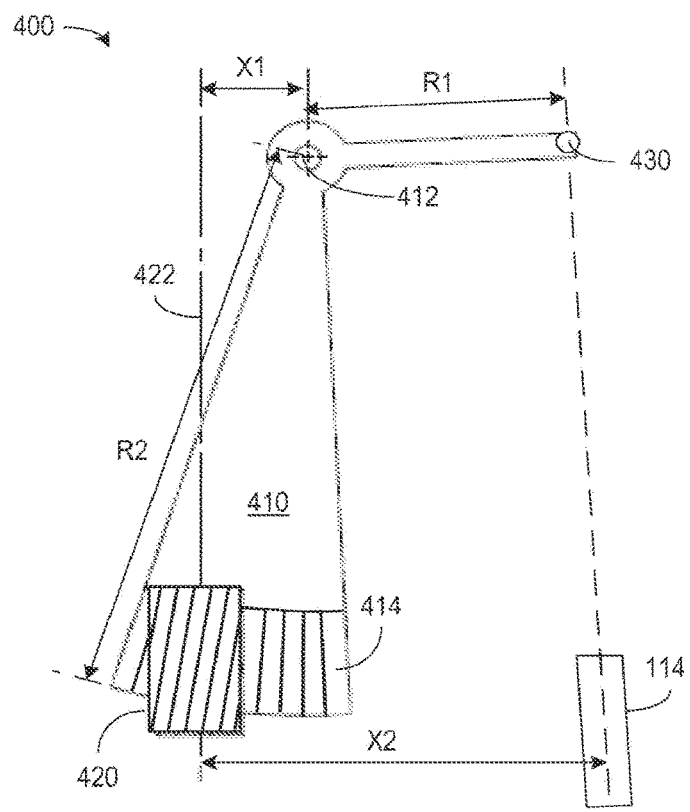
FIG. 4C schematically shows an arrangement of the pinion and face gear used in the actuation mechanism of FIGS. 4A and 4B.

Pinion 420 in the implementation shown in FIG. 4A is a helical gear, is cylindrical, and meshes with a flat toothed portion 414 of face gear 410 so that rotation axes of gears 410 and 420 do not intersect. FIG. 4C schematically illustrates the positions of face gear 410 and pinion 420 of mechanism 400 without other obscuring elements. As shown, a rotation axis of pinion 420 may be offset by a distance Xl from the rotation axis and shaft 412 of face gear 410. The helix angle of pinion 420 may be selected according to the tooth pattern of face gear 410, offset Xl, and a desired skew between the rotation axes 412 and 422 of face gear 410 and pinion 420. Alternative gear configurations or actuation mechanisms may use the same principles but vary offset Xl and the helix angle according to the space available for the actuation mechanism. Further, pinion 420 may be a cylindrical spur gear and tooth portion 414 of face gear 410 may be shaped to accommodate a spur gear as pinion 420. In still other implementations, gears 410 and 420 may be bevel gears. However, implementations in which pinion 420 is a cylindrical spur or a helical gear acting on a flat face gear 410 have the advantage of tolerance for vertical misalignment of input pinion 420 relative to face gear 410. Specifically, axial misalignment or shifting of pinion 420 along rotation axis 422 does not affect gear performance of actuation mechanism 400, which makes actuation mechanism 400 reliable and easy to assemble. Also, face gear 410 and a helical or spur input pinion 420 are straightforward to mold or cut from plastic or other material without requiring undercuts.

Figure 5:
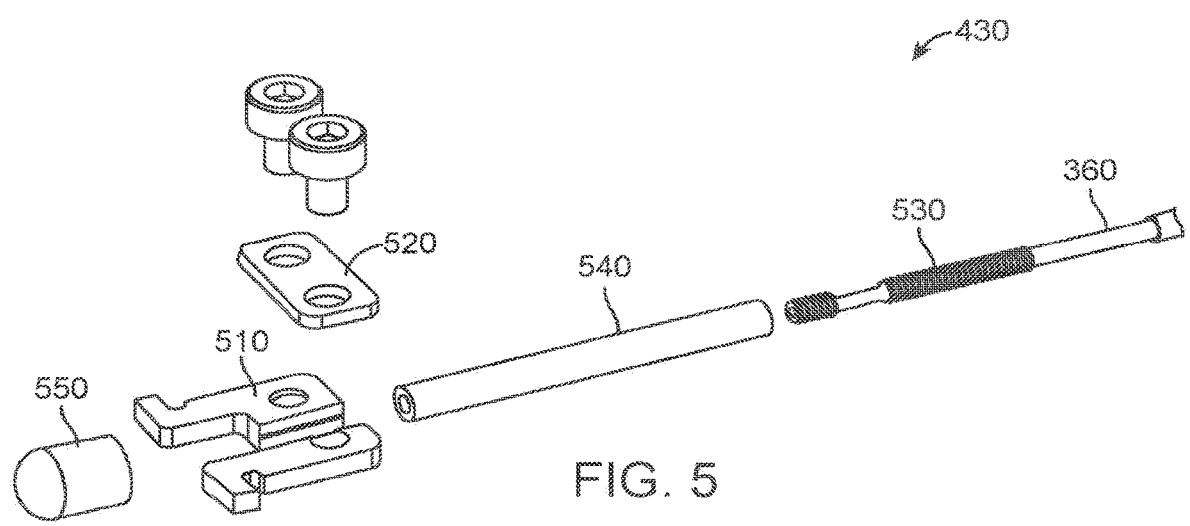
FIG. 5 shows an exploded view of an example implementation of a connector for connecting an actuation mechanism to push-pull element in a medical instrument.

An upper part of face gear 410 as shown in FIGS. 4A and 4B includes separated plates 416, and plates 416 connect to toothed portion 414 to create an arrangement with a "Y" or inverted "h" shape including a gap between plates 416. As described further below, the gap between plates 416 provides space for instruments components, e.g., cables and pulley systems, that need access to the instrument shaft. Plates 416 also accommodated connector 430, which may be mounted between plates 416 so that connector 430 can pivot and keep push-pull element 360 extending along the length axis of the instrument shaft. FIG. 5 shows an exploded view of one implementation of connector 430. In the implementation of FIG. 5, connector 430 includes a swing 510, which may be a stamped metal piece that snaps into notches in plates 416, and includes a clamp 520 that may bolt on to swing 510 to affix on swing 510 a metal grip rod 530 that is at the proximal end of push-pull element 360. An electrically insulating sheath 540 and an end cap 550 may be provided on grip rod 530 to electrically isolate push-pull element 360 from mechanical portions of the backend of the medical instrument, particularly when the distal grip mechanism may be electrically energized for cautery purposes.

Connector 430 attaches to face gear 410 at a moment arm or radius that may be selected according to the geometry of the instrument backend, e.g., according to a distance X2 between pinion 420 and instrument shaft 114. A radius R1 from rotation axis of face gear 410 to connector 430 may similarly be selected according to locations of face gear shaft 412 and instrument shaft 114. The mechanical advantage that actuation mechanism 400 may provide generally depends on radius R1 at which connector 430 attaches to face gear 410, a radius R2 of face gear 410, and a gear ratio between face gear 410 and pinion 420. Since radius R2 may be significantly larger than radius R1 and face gear 410 may be significantly larger than pinion 420, actuation mechanism 400 can achieve a relatively high mechanical advantage so that the mechanical advantage for a particular implementation may be selected from a large range. Implementations of grip actuation mechanisms disclosed herein can provide many further advantages over prior systems. In particular, actuation mechanism 400 may provide a lower sliding friction than a mechanism using worm or crossed helical gears, so that actuation mechanism is back-drivable. In particular, direct movement of a grip mechanism can drive movement of actuation mechanism 400. This allows a user to directly position a grip mechanism of a medical instrument without damaging the medical instrument. Grip actuation mechanism 400 also has geometric flexibility as described above to accommodate offsets and angles between instrument shaft 114 and input spindle 225 since the section of face gear 410 used and the helix angle of pinion 420 may be adjusted to shift the location and angle of the pinion relative to the axis of instrument shaft 114.

Figure 6:
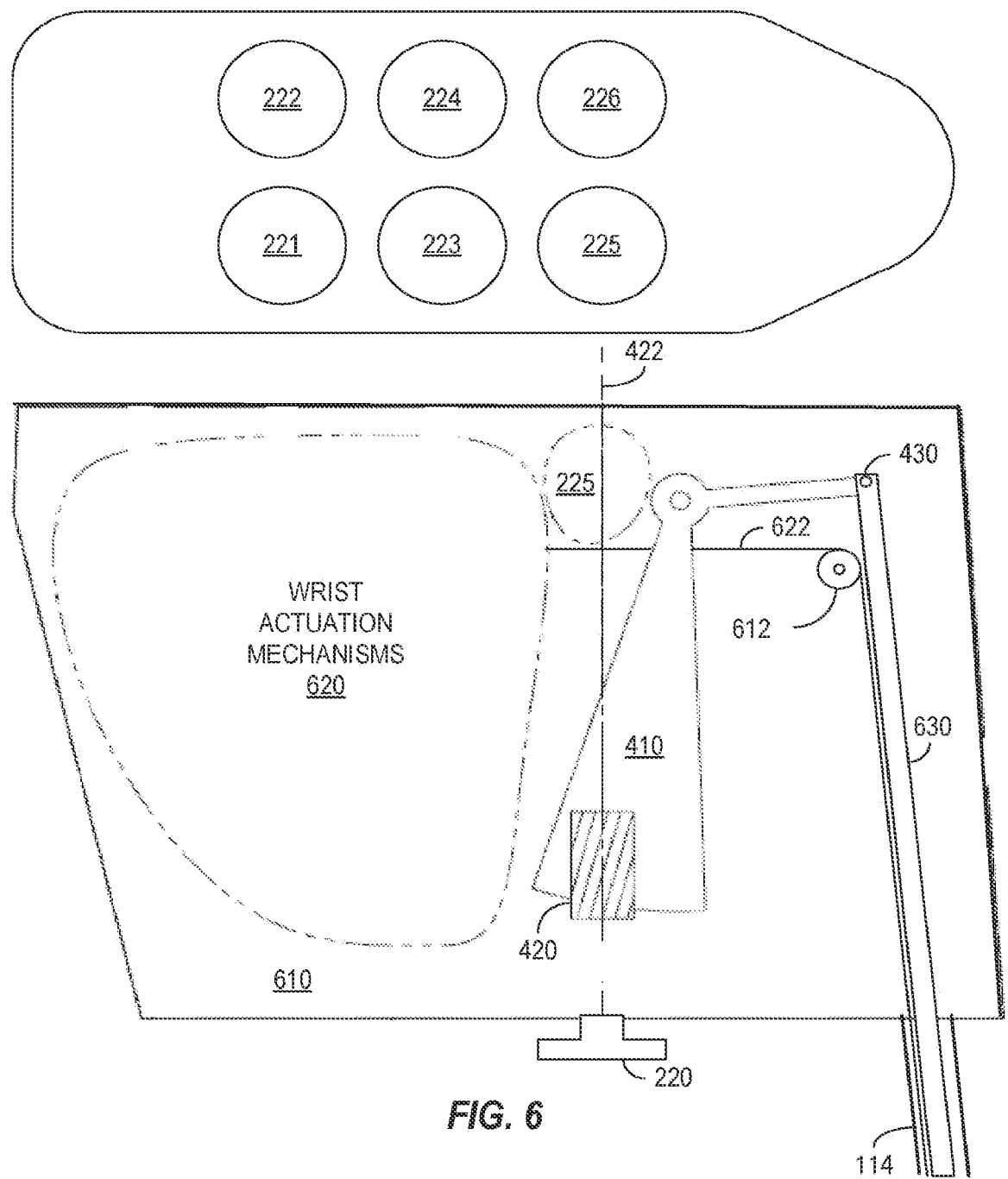
FIG. 6 shows structure in a backend of an example implementation of a medical instrument containing the actuation mechanism of FIGS. 4A and 4B.

The configuration of plates 416 of face gear 410 in addition to facilitating connection of connector 430 and push-pull element 360 to face gear 410 also creates a gap or opening near the top of face gear 410, permitting access through face gear 410 to the instrument shaft of a medical instrument. FIG. 6 schematically shows top and transparent side views of an example of an instrument backend in which the grip actuation mechanism of FIG. 4C is mounted within a chassis 610. In this implementation, chassis 610 also contains input spindle 226 with an associated roll action mechanism (not shown) and contains actuation mechanisms 620 associated with input spindles 221 to 224 that control cables 622 for actuation of wrists or joints of the instrument. The gap between plates 416 shown in FIGS. 4A and 4B allows routing of cables 622 between plates 416 to instrument shaft 114 and further provides space for pieces of chassis 610 and idler gears 612 that guide cables 622 toward instrument shaft 114. Co-filed U.S. Prov. Pat. App. No. 62/362,431, entitled "MULTI-CABLE MEDICAL INSTRUMENT," which is incorporated by reference herein in its entirety, further describes cable routing and a multi-piece chassis structure suitable for use with grip actuation mechanism disclosed herein.

Chassis 610 may hold input spindles 221 to 226 in position for engagement with a docking port on a robotic medical instrument such as described above with reference to FIG. 1. Input spindles 221 to 226 may each comprise an input shaft. Chassis 610 also positions manipulator 220 for user access and manual rotation of pinion 420, so that a user of a medical instrument may manually open or close the jaws of a medical instrument when the medical instrument is in hand instead of being attached to a robotic system. A user may need to manually open the jaws of a medical instrument, for example, to allow access to the inside and base of the jaws for cleaning of the jaws. In another case, a user may need to install a surgical clip or other medical device in the jaws of a medical instrument before docking the medical instrument on the robotic system when the medical instrument is to be used apply the surgical clip or other medical device. A user may also need to manually open the grips to release a clip or tissue in an emergency when an automated or robotic system is non-functional. A problem with manual operation of a grip actuation mechanism is that the torque manually applied through grip actuation mechanism may not be well controlled, and pushing on push-pull element 360 with too much force may cause element 360 to buckle or kink, thereby damaging the medical instrument. To avoid instrument damage, a slip clutch may be used to connect manipulator 220 to input spindle 225.

Figure 7A:
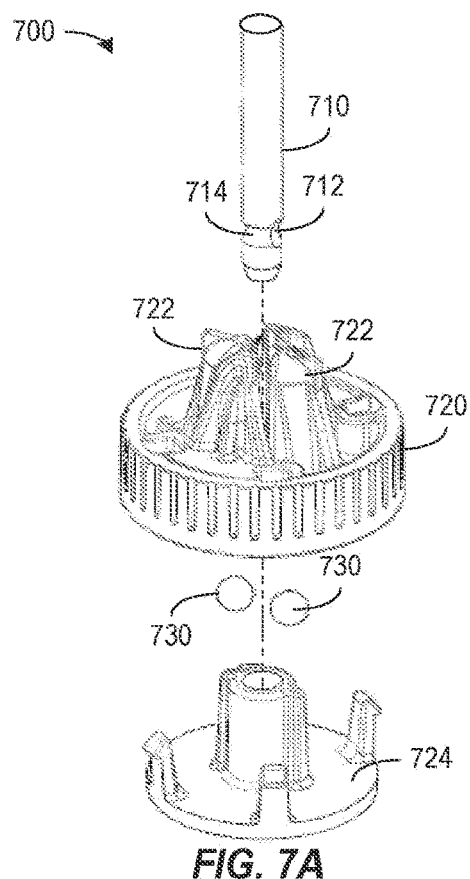
FIG. 7A is an exploded view of an example implementation of a manipulator suitable for manual operation of an actuation mechanism and including a slip clutch.
Figure 7B:
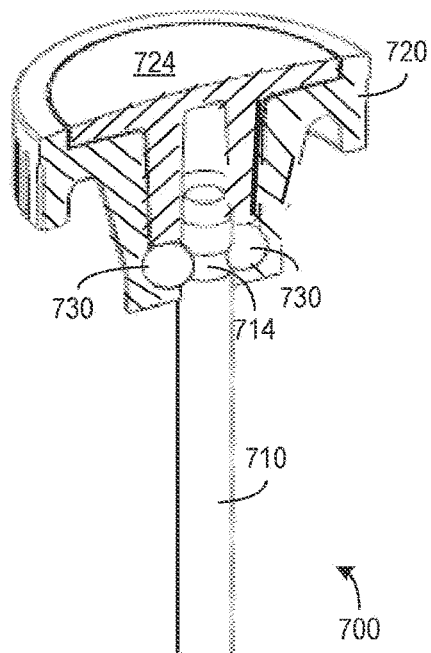
FIG. 7B shows a partial cross-sectional view of the manipulator of FIG. 7A when assembled.

FIG. 7A shows an exploded view of one implementation of a manipulator 700 with a slip clutch. For the slip clutch of FIG. 7A, a shaft or axle 710 of input spindle 225 includes one or more notches 712 that may reside in a groove 714 around a circumference of axle 710. Axle 710 fits into central bore in a knob 720. Knob 720 further has main piece including one or more flexures 722, and the main piece may be shaped for mounting of one or more plungers 730, e.g., ball bearings, rollers, or other structures having rounded or angled tips, in or on flexures 722. A knob cap 724 may fit into the main piece of knob 720 to hold plungers 730 in place. Axle 710 when inserted in knob 720 as shown in FIG. 7B may be positioned so that flexures 722 press plungers 730 into notches 712. Each notch 712 may be sized and shaped to accommodate a portion or a tip of a plunger 730, e.g., less than half, of a spherical surface of a plunger 730. When a user turns the assembled manipulator 700 of FIG. 7B, tips of plungers 730 in notches 712 may apply torque to rotate axle 710 with knob 720, but if axle 710 resists rotation, the tips of plungers 730 may lift out of notches 712 and slip, e.g., roll along groove 714, when reactive force arising from the torque applied to axle 710 overcomes the force with which flexures 722 press plungers 730 into notches 712. Accordingly, manipulator 700 may slip on axle 710 if the torque applied through knob 720 is too high.

Figure 8:
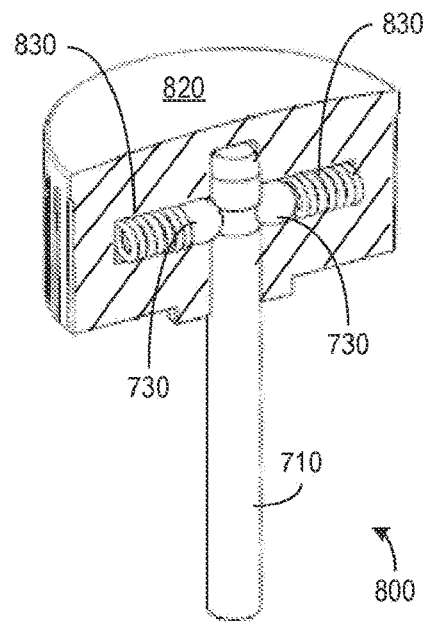
FIG. 8 shows a partial cross-sectional view of an example implementation of a manipulator with a slip clutch using springs to engage a plunger with an input drive shaft.

FIG. 8 shows an alternative implementation of a manipulator 800 including a slip clutch that allows a knob 820 to slip on an axle 710 when a user applies a large torque through knob 820. Manipulator 800, like manipulator 700 described above, uses plungers 730 that partially fit in notches in axle 710, but knob 820 uses springs 830 to press plungers 730 into the notches. Springs 830 may, for example, be coil or other metal springs. Otherwise, manipulator 800 works in the same fashion as manipulator 700, and the tips of plungers 730 may lift out of the notches and slip along the circumference of axle 710 when the reactive force arising from the torque applied through knob 820 overcomes the force with which springs 822 press the tips of plungers 730 into the notches in axle 710.

Figure 9A:
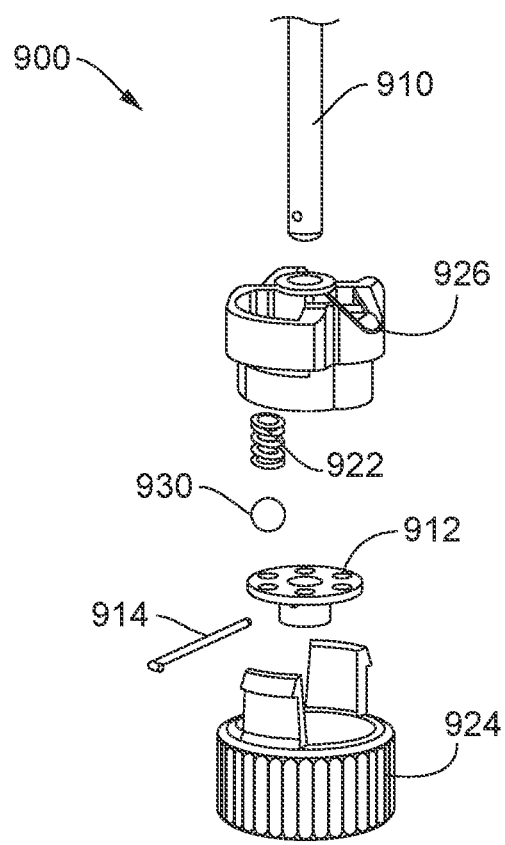
FIGS. 9A and 9B respectively show exploded and cross-sectional views of an example implementation of a manipulator with a slip clutch using springs to engage a plunger with a notched plate.
Figure 9B:
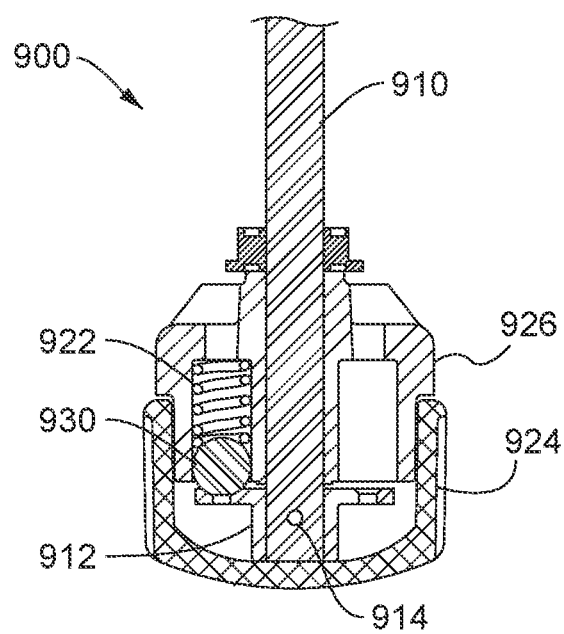

FIGS. 9A and 9B respectively show exploded and cross-sectional views of yet another alternative implementation of a manipulator 900 with a slip clutch. Manipulator 900 may attach to an axle 910 of an input spindle in the backend of a medical instrument such as disclosed above. In particular, axle 910 may be inserted through a bore in a knob insert 926, and a plate 912 may be attached to an end of axle 910 below knob insert 926. FIGS. 9A and 9B illustrate how a pin 914 may be used to attach plate 912 to axle 910 but many other types of attachments could be alternatively used. Plate 912 includes one or more notches that are sized to accommodate a tip of a plunger 930. One or more plunger 930 may be installed with a spring 922 in respective pockets in knob insert 926. A knob cap 924 may clip onto knob insert 926 to hold plate 912 in a position in which the plunger springs 922 are partly compressed. Manipulator 900 provides a slip clutch that enables manual rotation of knob cap 924 and axle 910 when the applied torque is insufficient to force plungers 930 out of the notches in plate 912, but when a greater torque is applied plungers 930 may slip out of the notches in plate 912 so that manipulator 900 slips relative to axle 910.

Figure 10:
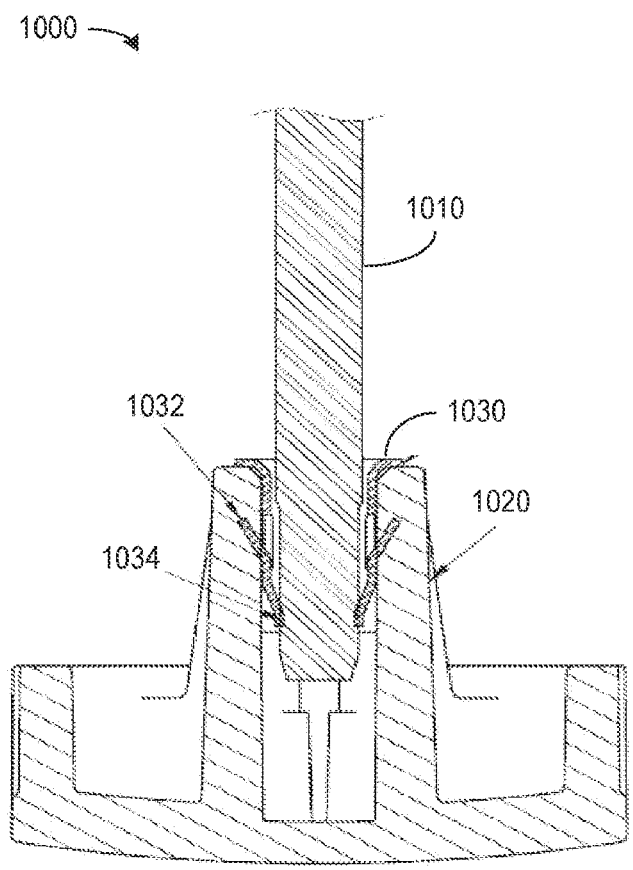
FIG. 10 shows a cross-sectional view of an example implementation of a manipulator with a slip clutch using clip that is friction fit on an input drive shaft.

FIG. 10 shows a manipulator 1000 that attaches an axle 1010 to a knob 1020 using a tubular clip 1030 that is friction fit on axle 1010. Clip 1030 includes features 1032 that grip into sides of knob 1020 to securely hold knob 1020 and clip 1030 together and prevent rotation of knob 1020 relative to clip 1030. Clip 1030 further includes features 1034 that grip axle 1010 to provide the friction fit with some pre-load so that rotation of knob 1020 rotates axle 1010 as long as the torque applied to axle 1010 is insufficient to overcome static friction between features 1034 and axle 1010, but knob 1020 slips relative to axle 1010 if the applied torque overcomes the friction between clip 1030 and axle 1010.

The mechanism described above have primarily been disclosed in the context of grip actuation but may be used for actuation of other degrees of freedom in an instrument such as a medical instrument. In particular, some disclosed implementations provide drive or actuation force in both pulling and pushing directions. While this feature is particularly desirable for grip motion or actuation, actuation of other types of instrument movement may also benefit from use of the mechanisms disclosed. In addition, although the above examples and other discussions herein often refer to medical procedures and medical instruments, the techniques disclosed also apply to non-medical procedures and non-medical instruments.

Although particular implementations have been disclosed, these implementations are only examples and should not be taken as limitations. Various adaptations and combinations of features of the implementations disclosed are within the scope of the following claims.

What is claimed is:

1. A medical instrument, comprising:
    an instrument shaft;
    a mechanical structure coupled to the instrument shaft, the mechanical structure comprising:
        an engagement structure configured to be coupled to an actuator of an instrument control mechanism,
        an input member operably coupled to the engagement structure,
        a transfer member rotationally coupled to the input member,
        a manual manipulator configured to be operably coupled to the transfer member in a first configuration and operably decoupled from the transfer member in a second configuration, and
    a drive element operably coupled to the input member via the transfer member;
    wherein the engagement structure is configured to be driven by the actuator of the instrument control mechanism;
    wherein the input member is configured to be actuated by one of the actuator and the manual manipulator to cause the transfer member to rotate; and
    wherein rotation of the transfer member causes movement of the drive element.

2. The medical instrument of claim 1, wherein the drive element is one of a rod, a wire, or a cable.

3. The medical instrument of claim 1, wherein the transfer member is a rotating disc.

4. A medical instrument, comprising:
    an instrument shaft;
    a tool coupled to the instrument shaft;
    a mechanical structure coupled to the instrument shaft, the mechanical structure comprising:
        an engagement structure configured to be coupled to an actuator of an instrument control mechanism, an input member operably coupled to the engagement structure, a manual manipulator operatively coupled to the input member via a slip clutch, and wherein rotation of at least one of the actuator or the manual manipulator causes the input member to rotate; and wherein rotation of the input member causes movement of the tool.

5. The medical instrument of claim 4, wherein the slip clutch comprises:

a plunger; and a spring system that pushes the plunger into a notch defined in the input member.

6. The medical instrument of claim 5, wherein:

the manual manipulator comprises a knob; and the spring system comprises a flexure formed in the knob and positioned to push the plunger into the notch.

7. The medical instrument of claim 2, wherein the drive element is routed from the mechanical structure into the instrument shaft.

8. The medical instrument of claim 1, wherein rotation of the input member causes rotation of the transfer member to cause movement of the drive element.

9. The medical instrument of claim 8, wherein:

the transfer member is configured to rotate about a rotation axis; and the drive element is coupled to the transfer member via a connector at a connection radius from the rotation axis.

10. The medical instrument of claim 1, wherein the manual manipulator may be actuated when the engagement structure is coupled to the actuator of the instrument control mechanism.

11. The medical instrument of claim 1, wherein the manual manipulator may be actuated when the engagement structure is decoupled from the actuator of the instrument control mechanism.

12. The medical instrument of claim 10, wherein the manual manipulator is any one of a knob, a lever, or a handle.

13. The medical instrument of claim 1, wherein the mechanical structure further comprises a clutch mechanism between the manual manipulator and the input member.

14. The medical instrument of claim 13, wherein the clutch mechanism is a slip clutch to limit an amount of torque transferred from the manual manipulator to the input member.

15. A medical instrument, comprising:

an instrument shaft;

a mechanical structure coupled to the instrument shaft, the mechanical structure comprising:

an engagement structure configured to be coupled to an actuator of an instrument control mechanism, an input member operably coupled to the engagement structure, a transfer member rotationally coupled to the input member, a manual manipulator configured to be operably coupled to the transfer member, and a clutch between the manual manipulator and the transfer member, the clutch configured to limit transfer of a torque between the manual manipulator and the transfer member, and a drive element operably coupled to the input member via the transfer member;

wherein the input member is configured to be actuated by one of the actuator of the instrument control mechanism and the manual manipulator to cause the transfer member to rotate; and wherein rotation of the transfer member causes movement of the drive element.

16. The medical instrument of claim 15, wherein:

the transfer member is configured to rotate about a rotation axis; and the drive element is coupled to the transfer member via a connector at a connection radius from the rotation axis.

17. The medical instrument of claim 15, wherein the drive element is one of a rod, a wire, or a cable.

18. The medical instrument of claim 17, wherein the drive element is routed from the mechanical structure into the instrument shaft.

19. The medical instrument of claim 15, wherein the manual manipulator may be actuated when the engagement structure is coupled to the actuator of the instrument control mechanism.

20. The medical instrument of claim 15, wherein the manual manipulator may be actuated when the engagement structure is decoupled from the actuator of the instrument control mechanism.

* * * * *